United States Patent [19]
Arakawa et al.

[11] Patent Number: 5,591,521
[45] Date of Patent: Jan. 7, 1997

[54] Z-SHAPE PRESSURE-SENSITIVE ADHESIVE TAPES, AND FASTENING SYSTEM AND SANITARY ABSORPTIVE ARTICLES USING THE TAPES

[75] Inventors: Masaaki Arakawa; Katsumi Hori; Yoshiaki Makihara, all of Osaka, Japan

[73] Assignee: Nitto Denko Corporation, Osaka, Japan

[21] Appl. No.: 323,106

[22] Filed: Oct. 14, 1994

[30] Foreign Application Priority Data

Oct. 15, 1993 [JP] Japan ........................ 5-258192
Sep. 20, 1994 [JP] Japan ........................ 6-224549

[51] Int. Cl.$^6$ ........................................ C09J 7/02
[52] U.S. Cl. ..................... 428/352; 428/354; 604/373; 604/389; 604/390
[58] Field of Search .................. 604/390, 389, 604/373; 428/352, 354, 343; 427/208, 208.4

[56] References Cited

U.S. PATENT DOCUMENTS

| | | | |
|---|---|---|---|
| 3,646,937 | 3/1972 | Gellert | 604/390 |
| 3,930,502 | 1/1976 | Tritsch . | |
| 4,047,529 | 9/1977 | Karami | 604/390 |
| 4,127,132 | 11/1978 | Karami . | |
| 4,177,812 | 12/1979 | Brown et al. | 604/373 X |
| 4,237,890 | 12/1980 | Laplanche | 428/261 |
| 4,299,223 | 11/1981 | Cronkrite | 604/390 |
| 4,650,483 | 3/1987 | Joffe | 604/390 |
| 5,182,156 | 1/1993 | Pape et al. | 604/390 X |

FOREIGN PATENT DOCUMENTS

| | | |
|---|---|---|
| 0520087 | 12/1992 | European Pat. Off. . |
| 2267058 | 4/1975 | France . |
| 3440544 | 11/1984 | Germany . |
| 52-47769 | 12/1977 | Japan . |
| 58-30401 | 6/1983 | Japan . |
| 1-56163 | 11/1989 | Japan . |
| 1441567 | 7/1976 | United Kingdom . |

*Primary Examiner*—Jenna Davis
*Attorney, Agent, or Firm*—Sughrue, Mion, Zinn, Macpeak & Seas

[57] ABSTRACT

A Z-shape pressure-sensitive adhesive tape folded into a Z-shape and composed of an (a) portion, a (b) portion, and a (c) portion, wherein a releasing treatment layer is formed on the outside surface of the (a) portion of the Z-shape tape and the surface of the (b) portion continuing the (a) portion at an area of not more than 50% of the total surface thereof, a releasing treatment layer does not exist on the inside surface of the (c) portion, and a pressure-sensitive adhesive layer is formed on at least one surface of the inside surface of the (a) portion and the outside surface of the (c) portion.

16 Claims, 8 Drawing Sheets

Z-SHAPE PRESSURE-SENSITIVE ADHESIVE TAPES, AND FASTENING SYSTEM AND SANITARY ABSORPTIVE ARTICLES USING THE TAPES

FIELD OF THE INVENTION

The present invention relates to Z-shape pressure-sensitive adhesive tapes which are suitably used as fixing tapes for various articles, absorptive articles such as, for example, paper diapers, napkins, and other sanitary articles, disposable articles such as body warmers, etc., and fastening tapes for fixing clothes, etc., and fastening systems and sanitary absorptive articles using the pressure-sensitive adhesive tapes.

BACKGROUND OF THE INVENTION

Hitherto, as fixing tapes for, for example, paper diapers, etc., various pressure-sensitive adhesive tapes constituted in a Z-shape are known as described, e.g., in JP-B-58-30401, JP-B-52-47769, and JP-B-1-56163 (the term "JP-B" as used herein means an "examined published Japanese patent application").

In particular, the Z-shape pressure-sensitive adhesive tape described in JP-B-58-30401 is folded such that a 1st leg (c) portion, a 2nd leg (b) portion, and a 3rd leg (a) portion are constituted but a releasing treatment layer to the adhesive formed on the 3rd leg (a) portion is formed on the surface only of the 2nd leg (b) portion and a releasing treatment layer is not formed on the outside surface of the 3rd leg (a) portion. Accordingly, when such a tape is wound in a roll form, rewinding becomes impossible and a separator is required, which give the problem that the pressure-sensitive adhesive tape is inferior in the productivity and the economy.

Also, since in the foregoing pressure-sensitive adhesive tape, the 1st leg (c) is stuck to the 3rd leg (a) with an adhesive by forming a penetrated hole at the central portion of the 2nd leg (b) portion, there are problems that the adhesive is exuded through such a penetrated hole to make rewinding impossible and the tape becomes sticky at use to give an unpleasant feeling to the consumers. Furthermore, it is proposed to form a Z-shaped tape by connecting the 1st leg portion to the 3rd leg portion by the pressure-sensitive adhesive layer of each pressure-sensitive adhesive tape each other as described in JP-B-52-47769. However, in this case, there are faults that owing to the adhesion by the pressure-sensitive adhesives each other, the adhesion is deteriorated by heat and with the passage of time and is liable to be disconnected and also when ordinary a strong shearing force or a strong releasing force is applied, the adhered portion is peeled and released.

SUMMARY OF THE INVENTION

The present invention has been made for solving the problems in the conventional techniques described above. That is, according to the present invention, there is provided a Z-shape pressure-sensitive adhesive tape folded into a Z-shape and composed of an (a) portion, a (b) portion, and a (c) portion, wherein a releasing treatment layer is formed on the outside surface of the (a) portion of the Z-shape tape and on the surface of the (b) portion continuing to the (a) portion at the area of not more than 50% of the whole area of the surface of the (b) portion, a releasing treatment layer does not exist on the inside surface of the (c) portion, and each of pressure-sensitive adhesive layers is formed on at least one surface of the inside surface of the (a) portion and the outside surface of the (c) portion.

DETAILED DESCRIPTION OF THE INVENTION

Then, the present invention is explained in detail by referring to the accompanying drawings.

Figure 1:
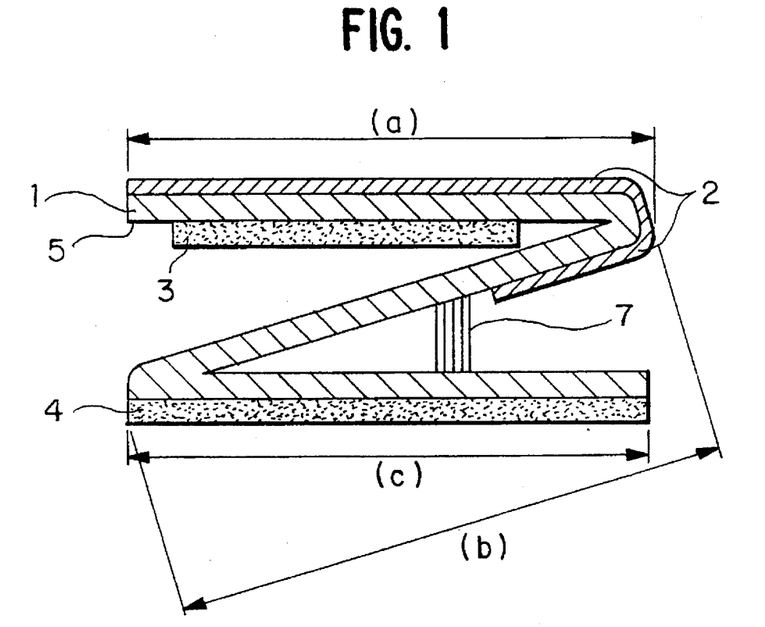
FIG. 1 is a cross sectional view showing a 1st embodiment of the Z-shape pressure-sensitive adhesive tape of the present invention.

FIG. 1 is a cross sectional view showing an embodiment of the Z-shape pressure-sensitive adhesive tape of the present invention, wherein a base material 1 is folded into a Z-shape to form an (a) portion, a (b) portion, and a (c) portion and a releasing treatment layer 2 is formed on the outside surface of the (b) portion and on the surface of the (b) portion continuing to the (a) portion. In this embodiment, a releasing treatment layer is not formed on the inside surface of the (c) portion. Also, each of pressure-sensitive adhesive layers 3 and 4 is formed on the inside surface of the (a) portion and on the outside surface of the (c) portion. Furthermore, the surface of the (b) portion where the releasing treatment layer 2 does not exist is temporarily joined to the inside surface of the (c) portion by a temporary joining means 7 (described below).

The releasing treatment layer 2 described above is formed on the surface of the (b) portion at the area of not more than 50%, and preferably from about 1 to 20% of the whole surface area. If the releasing treatment layer 2 exists on the whole surface of the (b) portion, the temporary joining means for joining the (b) portion to the (c) portion cannot be formed and also the cost is increased. On the other hand, if no releasing treatment layer 2 exists on the surface of the (b) portion, it is undesirable that the end of the pressure-sensitive adhesive layer 4 of the (c) portion is protruded, whereby the (b) portion is stuck to the (c) portion and there is a possibility that the tape cannot be pulled out.

Figure 2:
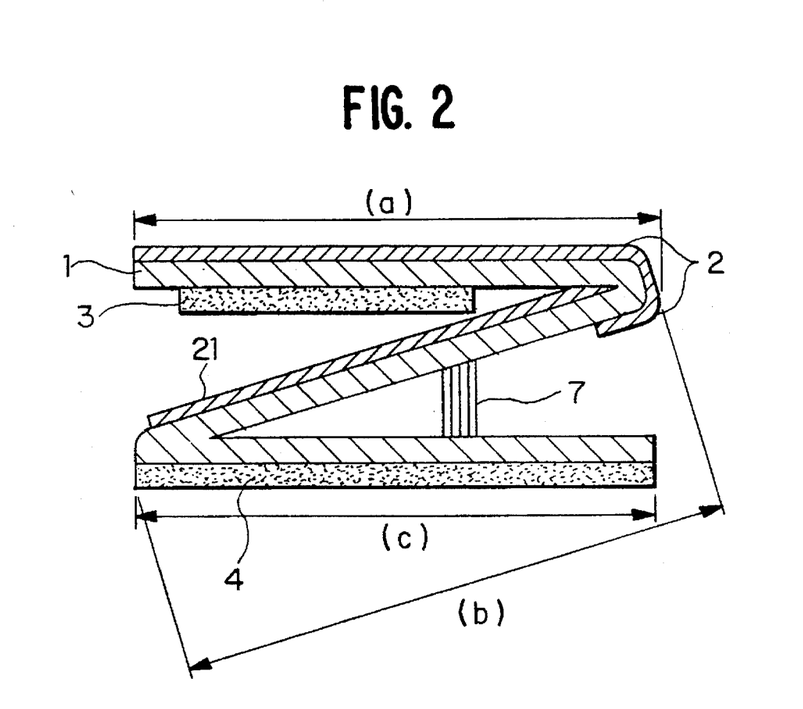
FIG. 2 is a cross sectional view showing a 2nd embodiment of the Z-shape pressure-sensitive adhesive tape of the present invention.

Also, as shown in FIG. 2, by further forming a releasing treatment layer 21 on the back surface side of the (b) portion to the surface having the releasing treatment layer 2 of the (b) portion continuing the releasing treatment layer 2 of the (a) portion, that is, on the surface of the (b) portion facing the pressure-sensitive adhesive layer 3 of the (a) portion, the (a) portion can be easily released from the (b) portion in the case of pulling out the Z-shape pressure-sensitive adhesive tape.

However, according to the nature of the pressure-sensitive adhesive layer 3, the (a) portion can be easily released from the portion (b) without need of the releasing treatment layer 21 as shown in FIG. 1.

Figure 3:
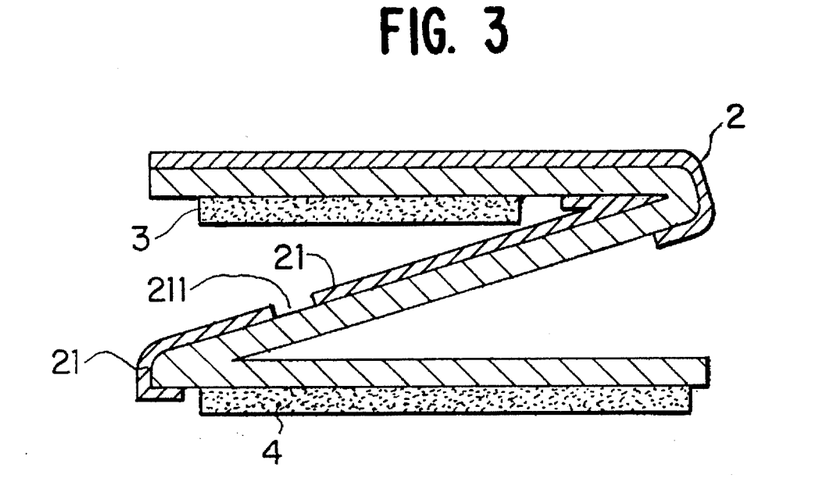
FIG. 3 is a cross sectional view showing a 3rd embodiment of the Z-shape pressure-sensitive adhesive tape of the present invention.

Also, it is preferred that the left end position of the pressure-sensitive layer 3 of the (a) portion may be same as the left end position of the pressure-sensitive adhesive layer 4 of the (c) portion as shown in FIG. 3 or is retreated a little to the right side as shown in FIG. 1. By employing such a mode, there is no possibility that the pressure-sensitive adhesive layer 3 of the (a) portion is stuck to the pressure-sensitive adhesive layer 4 of the (c) portion.

In the embodiment shown in FIG. 3, the releasing treatment layer 21 formed on the surface of the (b) portion folded into a Z-shape facing the pressure-sensitive adhesive layer 3 of the (a) portion is also formed on the inside surface of the (a) portion at an area of not more than 30% of the inside surface of the (a) portion and on the outside surface of the (c) portion at an area of not more than 30% of the outside surface of the (c) portion as a continuing layer. By employing such a mode, it can be prevented that the pressure-sensitive adhesive layer 3 of the (a) portion is stuck to the surface of the (b) portion and they are reluctant to be released and also the occurrence of the adhesion of the pressure-sensitive adhesive layer 4 of the (c) portion and the pressure-sensitive adhesive layer 3 of the (a) portion can be prevented.

In the embodiment shown in FIG. 3, the releasing treatment layer 21 of the (b) portion has a lacked portion 211 where the layer does not partially exist and by forming such a lacked portion 211, the (a) portion is not each released from the (b) portion more than necessary.

Practically, it sometimes happens that the (a) portion of the Z-shape pressure-sensitive adhesive tape is taken off by the contact resistance in the case of putting an underwear or clothing on a diaper or taking off it from a diaper. Thus, as in the present invention, by forming the lacked portion 211 in the releasing treatment layer 21 of the (b) portion having partially no such layer, the pressure-sensitive adhesive layer 3 of the (a) portion can be weakly stuck to the (b) portion by the pressure-sensitive adhesive layer 3 and the lacked portion 211 partially having no releasing treatment layer, whereby the occurrence of taking off of the pressure-sensitive adhesive tape can be easily prevented even when the contact resistance occurs as described above.

Also, by forming a dry edge 5 at the inside surface of the left end portion of the (a) portion as shown in FIG. 1, the tape can be easily picked. The term "dry edge" as used herein means a portion not having a pressure-sensitive adhesive layer thereon.

Figure 4:
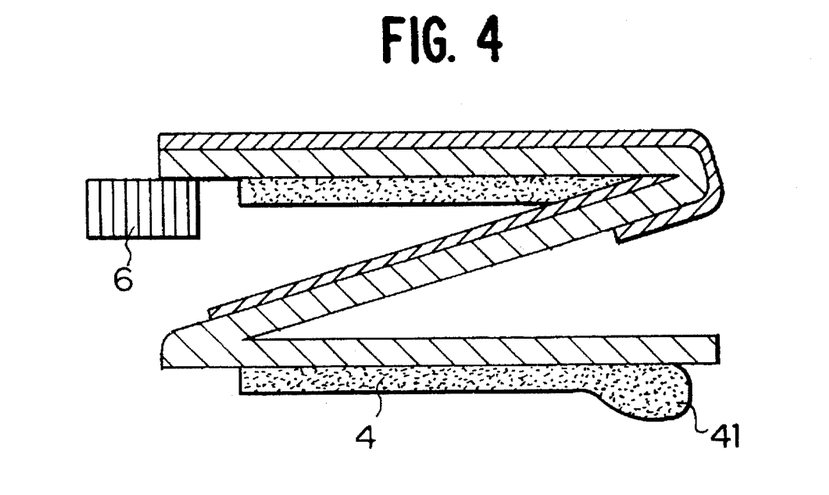
FIG. 4 is a cross sectional view showing a 4th embodiment of the Z-shape pressure-sensitive adhesive tape of the present invention.

Furthermore, by forming a picking portion 6 at the inside surface of the left end portion of the (a) portion as shown in FIG. 4, the facility of picking the tape can be improved and also, the step difference of the pressure-sensitive adhesive layer at the end portion of the (c) portion can be controlled, whereby the pressure-sensitive adhesive tape can be stably kept as a web or a roll form.

Also, by applying printing onto the outside surface of the end portion of the (a) portion to inform a user the picking portion, whereby the tape can be easily picked.

Figure 5:
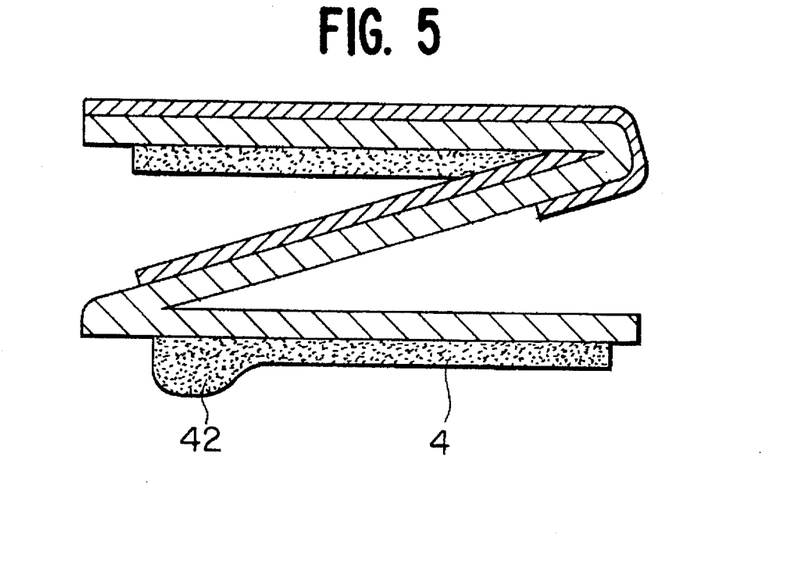
FIG. 5 is a cross sectional view showing a 5th embodiment of the Z-shape pressure-sensitive adhesive tape of the present invention.
Figure 13:
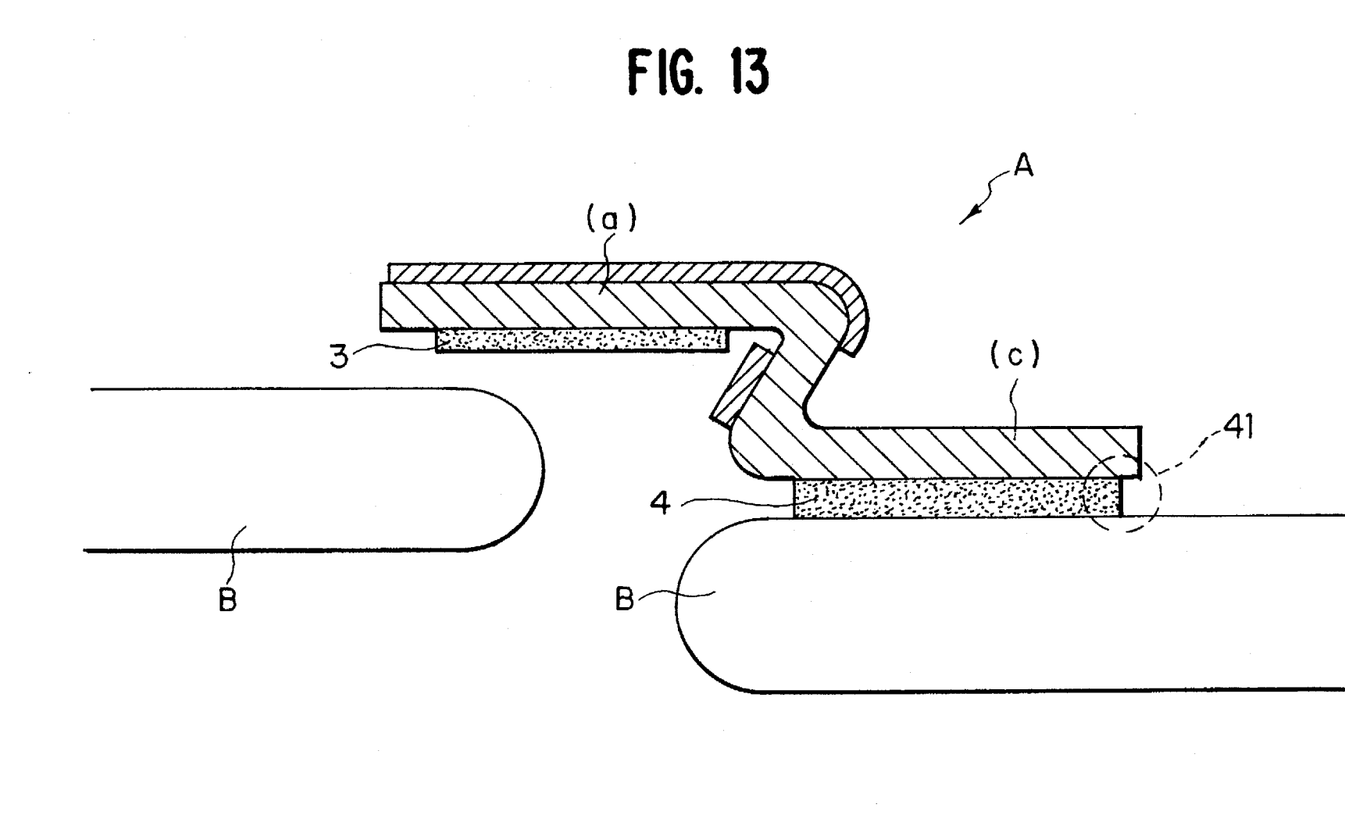
FIG. 13 is a schematic view showing a using mode of the Z-shape pressure-sensitive adhesive tape of the present invention.

Also, as shown in FIG. 4, by thickening the thickness of the right end portion 41 of the pressure-sensitive adhesive layer 4 formed on the outside surface of the (c) portion, when the Z-shape pressure-sensitive adhesive tape A is fixed to an article to be stuck, such as, a diaper as shown in Table 13, the adhesive power can be improved such that the tape can endure the stress to the shearing direction concentrated to the right end portion 41 of the pressure-sensitive adhesive layer 4 of the (c) portion of the pressure-sensitive adhesive tape A to reinforce the adhesion. Also, as shown in FIG. 5, by thickening the thickness of the left end portion 42 of the pressure-sensitive adhesive layer 4 formed on the outside surface of the (c) portion, there are advantages that when a user picks not only the end of the (a) portion only but also the (a) portion and the bent portion of the (b) (c) portions together by mistake and pulls them, the tape can be prevented from releasing from the attached article and further when a user pulls strongly the (a) portion upward by mistake, the tape can be prevented from releasing from the attached article by the concentration of stresses onto the bent portion of the (b) portion and the (c) portion.

Figure 6:
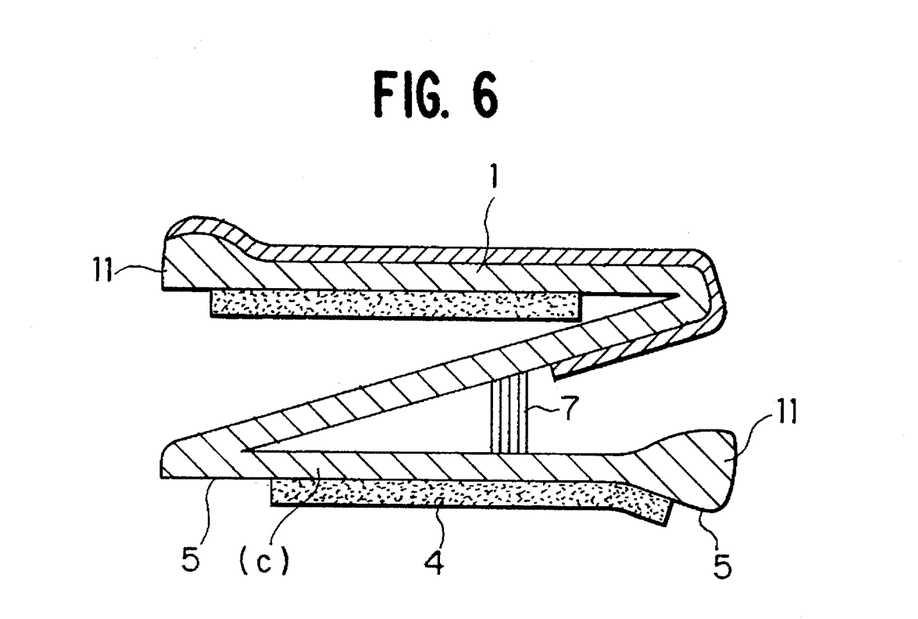
FIG. 6 is a cross sectional view showing a 6th embodiment of the Z-shape pressure-sensitive adhesive tape of the present invention.

FIG. 6 is a cross sectional view showing other embodiment of the Z-shape pressure-sensitive adhesive tape of the present invention and as shown in FIG. 6, by thickening the thickness of both the end portions 11 of the base material 1 or the thickness of one end portion of the base material 1, the adhesive force of the (c) portion to which stresses are concentrated as in the case described above can be improved to reinforce the adhesion.

Furthermore, in the processing line of the Z-shape pressure-sensitive adhesive tape of the present invention, the pressure-sensitive tape is fixed to an article such as a diaper, etc., by laminating or pressing and in this case, when the thickness of the base material is thicker, there is an advantage that the tape is more easily pressed and the tape can be sufficiently adhered.

Also, by forming a dry edge 5 at the outside surface of both the ends or one end of the (c) portion, the possibility that the end portion of the pressure-sensitive adhesive layer 4 of the (c) portion is protruded to adhere the (a) portion and the (c) portion, whereby the tape cannot be pulled out can be prevented.

Figure 7:
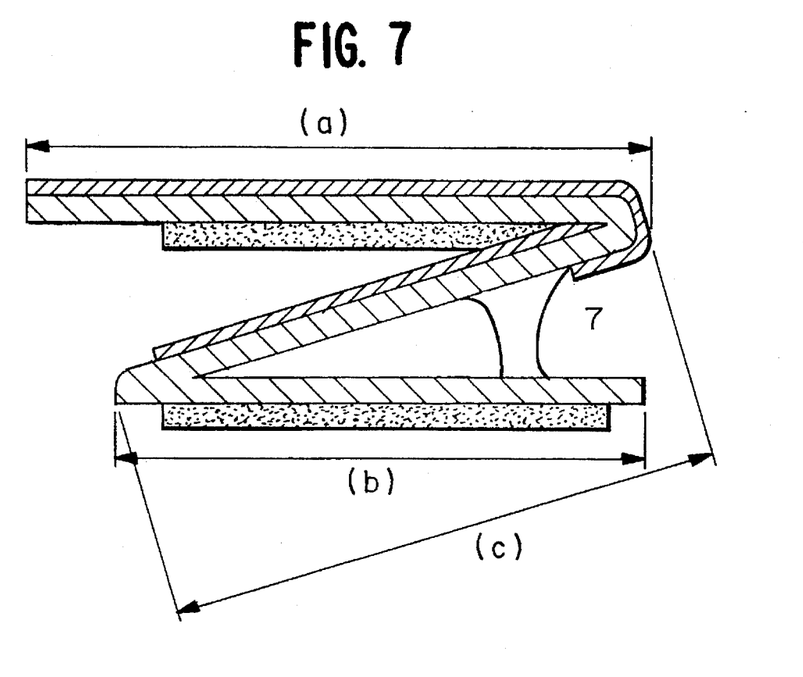
FIG. 7 is a cross sectional view showing a 7th embodiment of the Z-shape pressure-sensitive adhesive tape of the present invention.
Figure 8:
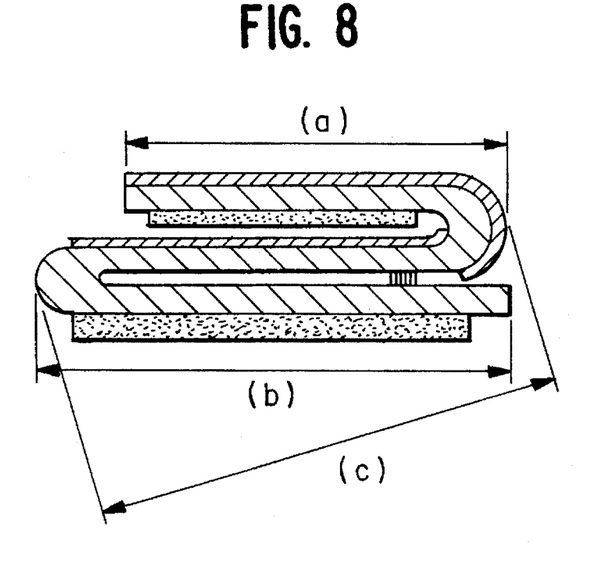
FIG. 8 is a cross sectional view showing a 8th embodiment of the Z-shape pressure-sensitive adhesive tape of the present invention.

In the present invention, it is preferred that as shown in FIG. 7, the length of the (a) portion is longer than those of the (b) portion and the (c) portion such that when the tape is folded into a Z-shape, the end of the (a) portion is projected over the bent portion of the (b) portion and the (c) portion. Or, alternatively, it is preferred that as shown in FIG. 8, the length of the (a) portion is shorter than those of the (b) portion and the (c) portion such that when the tape is folded into a Z-shape, the end of the (a) portion is retreated from the bent portion of the (b) portion and the (c) portion. By employing these embodiments, there is an advantage that when the (a) portion is pulled out, the (a) portion is easily picked by a user. If the lengths of the (a) portion, the (b) portion, and the (c) portion are same, there is a possibility of making an erroneous operation that in the case of pulling out the (a) portion, the bent portion of the (b) portion and the (c) portion is picked by fingers by mistake without picking the end portion of the (a) portion, whereby the Z-shape pressure-sensitive tape itself is released from the attached article.

In the present invention, there is further an advantage that as shown in FIG. 1, in the pressure-sensitive adhesive tape folded into a Z-shape and composed of the (a) portion, the (b) portion, and the (c) portion, by temporarily joining the inside surface of the (b) portion without having the releasing treatment layer 2 to the facing inside surface of the (c) portion, the Z-shape is not opened before using the tape.

There is no particular restriction on the temporary joining means 7 but, for example, the inside surface of the (b) portion without having the releasing treatment layer 2 can be temporarily joined by a heat seal, a hot melt type, melt blow type, or fibrous pressure-sensitive adhesive or adhesive, or an emboss system by press.

Figure 9:
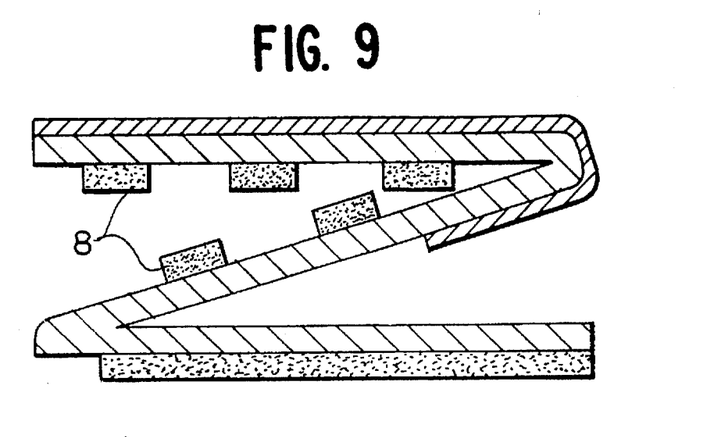
FIG. 9 is a cross sectional view showing a 9th embodiment of the Z-shape pressure-sensitive adhesive tape of the present invention.
Figure 10:
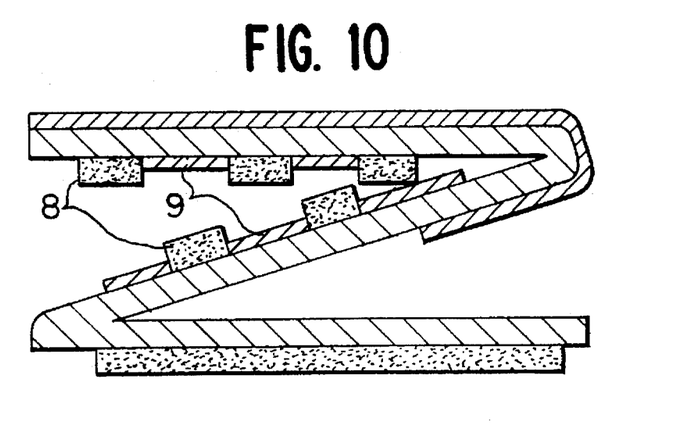
FIG. 10 is a cross sectional view showing a 10th embodiment of the Z-shape pressure-sensitive adhesive tape of the present invention.

Also, as shown in FIG. 9, by alternately forming the pressure-sensitive adhesive layers 8 on the inside surface of the (a) portion and the facing surface of the (b) portion, there is an advantage that the adhered portions extend to both the surfaces of the (a) portion and the (b) portion to more strengthen the fix. Furthermore, as shown in FIG. 10, the pressure-sensitive adhesive layers 8 and the releasing treatment layers 9 can be alternately formed on the inside surface of the (a) portion and the facing surface of the (b) portion.

Furthermore, in the present invention, it is preferred that the ratio of the releasing force of the releasing treatment layer 2 of the (a) portion to the pressure-sensitive adhesive layer 4 of the (c) portion to the releasing force of the releasing treatment layer 21 of the (b) portion to the pressure-sensitive adhesive layer 3 of the (a) portion is 1:1.2 or more. The reason is that in the case of rewinding the Z-shape pressure-sensitive adhesive tape of the present invention wound into a roll form, if both the releasing forces are same or the releasing force at the (b) portion side is weaker, there is a possibility of rewinding the Z-shape pressure-sensitive adhesive tape in an open state, which results in making the tape unusable.

Also, since if the releasing force of the (b) portion is too weak, when the tape is folded into a Z-shape, the (a) portion is easily released, it is preferable that the releasing force of the (b) portion is properly strengthened. For example, when the releasing force of the (a) portion is 100 g/25 mm, the releasing force of the (b) portion is preferably about 150 g/25 mm. The releasing force can be measured using a Tensilon type universal testing machine at a pulling rate of 300 mm/minute and a 180° peeling under the condition of a temperature of 23° C. and a relative humidity of 65%.

Furthermore, for users, it is preferred that the maximum releasing force of both the portions are not over 800 g/25 mm, and in particular from 100 to 200 g/25 mm from the point of easily releasability. Thus, it is also preferred that the releasing strength of the foregoing temporary joining means 7 is not over 800 g/25 mm from the same point as described above.

Figure 11:
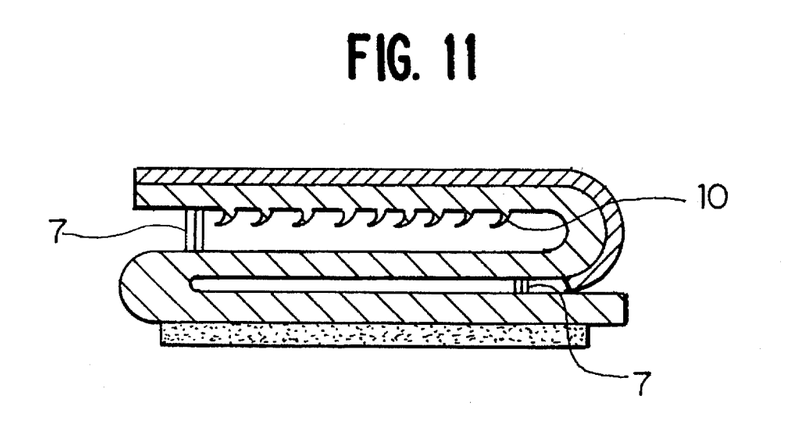
FIG. 11 is a cross sectional view showing a 11th embodiment of the Z-shape pressure-sensitive adhesive tape of the present invention.
Figure 12:
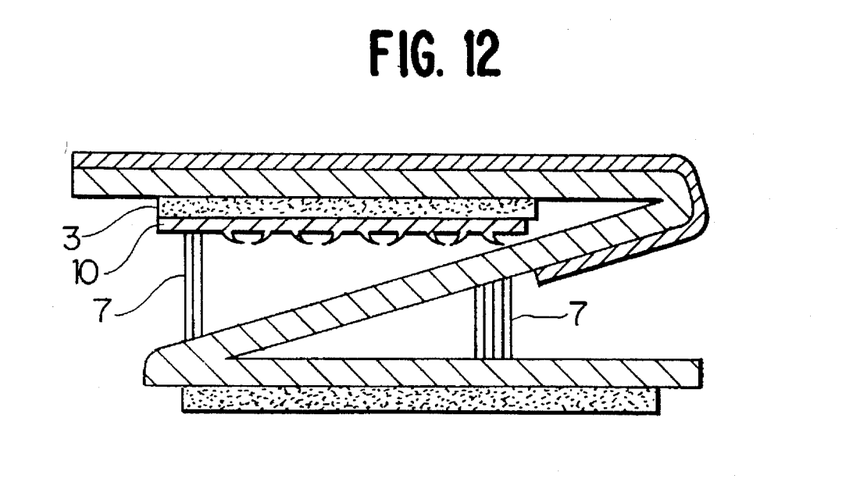
FIG. 12 is a cross sectional view showing a 12th embodiment of the Z-shape pressure-sensitive adhesive tape of the present invention.

Moreover, in the present invention, as shown in FIG. 11 or FIG. 12, by forming uneven hook-form fastening means 10 on the inside surface of the (a) portion or on the pressure-sensitive adhesive layer 3 of the (a) portion and temporarily joining the (a) portion and the (b) portion with the temporary joining means 7, the tape can be re-adhered to a fibrous or nonwoven fabric form sheet or a roop-form article to be fastened.

A Z-shape pressure-sensitive adhesive tape having a pressure-sensitive adhesive layer only either of one surface of the inside surface of the (a) portion and the outside surface of the (c) portion may be used after the surface not having a pressure-sensitive adhesive layer is processed by the end user to have a pressure-sensitive adhesive property or a double-coated pressure-sensitive adhesive layer is formed thereon.

The base material which can be used in the present invention is not limited, but examples thereof include a film or laminate of polyethylene, polypropylene, polyester or a blend thereof. A blend of polyethylene and propylene is particularly preferred.

The releasing agent to be used for the releasing treatment is not limited, but examples thereof include silicone series releasing agents and long-chain alkyl series releasing agents, with UV cure type silicone series releasing agents being particularly preferred.

As the pressure-sensitive adhesive to be used in the present invention, those mainly comprising a rubber such as natural rubber and synthetic rubber are preferred. For a hot melt coating not causing environmental pollution, those mainly comprising a ABA type or AB type block copolymer (where A and B represent a thermoplastic block and a rubber block, respectively) are preferred. Examples thereof include a styrene-isoprene-styrenecopolymer, a styrene-butadiene-styrene copolymer, a styrene-ethylene-butadiene-styrene copolymer, a styrene-butadiene copolymer and a hydrogenated product thereof.

In the case where the pressure-sensitive adhesive is a hot melt type, the pressure-sensitive adhesive can be coated by extruding. In the other cases, the pressure-sensitive adhesive can be coated in the form of a solution having the pressure-sensitive adhesive dissolved therein or an emulsion.

In a Z-shape pressure-sensitive adhesive tape A of the present invention, as shown in FIG. 13, the (c) portion is fixed to, e.g., the surface of a diaper B with the pressure-sensitive adhesive layer 4 and the (a) portion is pulled out and fixed to other portion of the diaper B.

Figure 14:
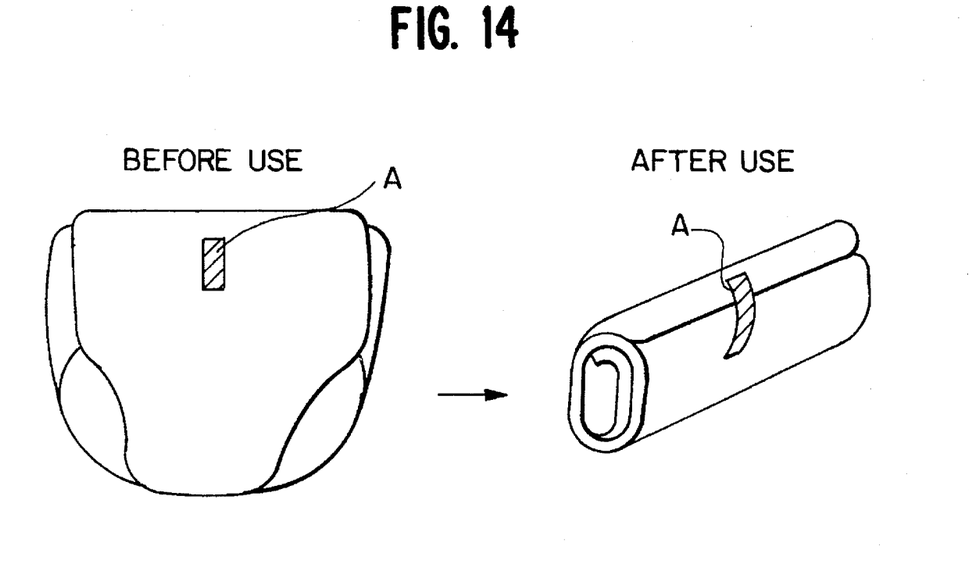
FIG. 14 is a schematic view showing other using mode of the Z-shape pressure-sensitive adhesive tape of the present invention.

Also, in a Z-shape pressure-sensitive adhesive tape A of the present invention, as shown in FIG. 14, the tape of the invention can be used as a tape for treating an underpants type diaper after use, for fixing the spoiled diaper after being coiled.

Figure 15:
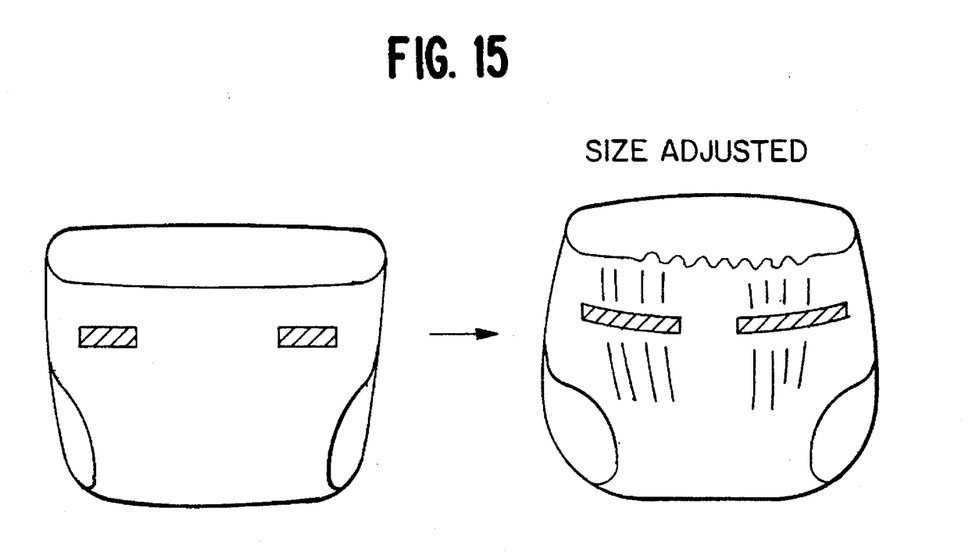
FIG. 15 is a schematic view showing another using mode of the Z-shape pressure-sensitive adhesive tape of the present invention.

Furthermore, when a large diaper is purchased such as, for example, when the growth of a baby is remarkable, as shown in FIG. 15, by spreading the Z-shape pressure-sensitive adhesive tape of the present invention and fixing it, the waist portion can be tightened and also the tape can be used for size controlling.

Then, the invention is further described practically by the following examples.

EXAMPLES

In the following examples, the tapes having the structure shown in FIG. 2 were prepared using a film (thickness: 100

μm) comprising a blend of polyethylene and polypropylene (50:50 by weight) and a rubber type pressure-sensitive adhesive (styrene-isoprene-styrene type) as a base material and a pressure-sensitive adhesive, respectively. The releasing treatment was carried out using a silicone type releasing agent.

Example 1

(Rewinding Test)

The Z-shape pressure-sensitive adhesive tape (500 m roll) of the present invention was subjected to a rewinding test of 10 meters/minute and in the test, the opening extent of the Z-shape tape for the releasing forces of the (a) portion and the (b) portion was determined. The results obtained are shown in Table 1 below.

TABLE 1

|  | Invention | | | | |
|---|---|---|---|---|---|
| Sample No. | 1 | 2 | 3 | 4 | 5 |
| (a) Portion Releasing Force (g/25 mm) | 100 | 100 | 100 | 100 | 100 |
| (b) Portion Releasing Force (g/25 mm) | 50 | 100 | 110 | 120 | 150 |
| (a)/(b) Ratio | 1/0.5 | 1/1 | 1/1.1 | 1/1.2 | 1/1.5 |
| Opening Extent | C | C | B | A | A |

Criterion
A: The (a) portion opened from the (b) portion.
B: The (a) and (b) portions opened slightly from each other.
C: The Z-shape was kept without opening the (a) and (b) portions.

Example 2

The Z-shape pressure-sensitive adhesive tape having the releasing force of the (b) portion and the releasing force of the temporary joining portion was tested by 12 persons and each term was evaluated by the 5 ranks shown below. The results obtained are shown in Table 2 below.

TABLE 2

|  | Invention | | | | | |
|---|---|---|---|---|---|---|
| Sample No. | 6 | 7 | 8 | 9 | 10 | 11 |
| (b) Portion Releasing Force (g/25 mm) | 50 | 200 | 400 | 600 | 800 | 1000 |
| Temporary Joining portion Releasing Force (g/25 mm) | 20 | 100 | 300 | 500 | 700 | 900 |
| Releasability | A | A | A | B | C | E |
| Expandability | A | A | A | B | C | E |
| Maintenance of | C | A | A | A | A | A |
| Total Evaluation | B | A | A | B | C | D |

Criterion
A: Good
B: Probably good
C: Ordinary
D: Not so good
E: No good

As described above, when the Z-shape pressure-sensitive adhesive tape of the present invention is wound in a roll form, the tape can be easily rewound without need of a separator and the tape has an advantage of excellent in the productivity and economy.

Also, there is no particular restriction on the uses of the tape but the tape of the present invention is suitably used as fixing tapes for various articles such as, for example, fastening tapes of fixing, paper diapers, napkins, absorptive articles such as sanitary articles, etc., disposable articles such as body warmers, etc., and clothes, etc.

In particular, the Z-shape pressure-sensitive adhesive tape of this invention is suitable as a disposal tape for fixing a spoiled underpants type diaper after being coiled.

While the invention has been described in detail with reference to specific embodiments, it will be apparent to one skilled in the art that various changes and modifications can be made to the invention without departing from its spirit and scope.

What is claimed is:

1. A Z-shape pressure-sensitive adhesive tape folded into a Z-shape and composed of an (a) portion, a (b) portion, and a (c) portion, wherein a releasing treatment layer is formed on the outside surface of the (a) portion of the Z-shape tape and the surface of the (b) portion extending to the (a) portion at an area of not more than 50% of the total surface thereof, a releasing treatment layer does not exist on the inside surface of the (c) portion, and a pressure-sensitive adhesive layer is formed on at least one surface of the inside surface of the (a) portion and the outside surface of the (c) portion wherein in the pressure-sensitive adhesive tape folded into a Z-shape and composed of the (a) portion, the (b) portion, and the (c) portion, the surface of the (b) portion, wherein the releasing treatment layer does not exist, is temporarily joined to the facing inside surface of the (c) portion.

2. A Z-shape pressure-sensitive adhesive tape of claim 1, wherein a releasing treatment layer is formed on the whole surface or a part of the surface of the (b) portion facing the inside surface of the (a) portion.

3. A Z-shape pressure-sensitive adhesive tape of claim 1 or 2, wherein a dry edge and/or a picking portion is formed at the inside surface of the left end portion of the (a) portion folded into a Z-shape.

4. A Z-shape pressure-sensitive adhesive tape of claim 1, wherein the thickness of the pressure-sensitive adhesive layer formed on the outside surface of the (c) portion folded into a Z-shape is thicker at both ends or one end of the layer.

5. A Z-shape pressure-sensitive adhesive tape of claim 1, wherein the thickness of the base material of the pressure-sensitive adhesive tape folded into a Z-shape and composed of the (a) portion, the (b) portion, and the (c) portion is thicker in both ends or one end of the base material than the center portion thereof.

6. A Z-shape pressure-sensitive adhesive tape of claim 1, wherein the outside surface of the (c) portion folded into a Z-shape becomes a dry edge at both ends or one end of the (c) portion.

7. A Z-shape pressure-sensitive adhesive tape of claim 1, wherein the end of the (a) portion folded into a Z-shape is projected or retreated from the bent portion of the (b) portion and the (c) portion.

8. A Z-shape pressure-sensitive adhesive tape of claim 2, wherein the releasing treatment layer formed on the surface of the (b) portion folded into a Z-shape facing the pressure-sensitive adhesive layer of the (a) portion has a portion wherein the layer does not partially exist.

9. A Z-shape pressure-sensitive adhesive tape of claim 1, wherein the releasing treatment layer formed on the surface of the (b) portion folded into a Z-shape facing the pressure-sensitive adhesive layer of the (a) portion is also formed on the inside surface of the continuing (a) portion and on the outer surface of the (c) portion at the area of not more than 30% of the inside surface of the (a) portion and the outside surface of the (c) portion, respectively.

10. A Z-shape pressure-sensitive adhesive tape of claim 1, wherein the left end position of the pressure-sensitive adhesive layer of the (a) portion is same as that of the pressure-sensitive adhesive layer of the (c) portion or is retreated to the right side of the pressure-sensitive adhesive layer of the (c) portion.

11. A Z-shape pressure-sensitive adhesive tape of claim 1, wherein the ratio of the releasing force of the releasing treatment layer of the (a) portion to the pressure-sensitive adhesive layer of the (c) portion to the releasing force of the releasing treatment layer of the (b) portion to the pressure-sensitive layer of the (a) portion is 1:1.2 or more.

12. A Z-shape pressure-sensitive adhesive tape of claim 1, wherein the temporary joining means is a heat seal, an adhesive, or a pressure-sensitive adhesive.

13. A Z-shape pressure-sensitive adhesive tape of claim 1, wherein hook-form fastening means are formed on the surface of the (a) portion itself or through the pressure-sensitive adhesive layer of the (a) portion.

14. A Z-shape pressure-sensitive adhesive tape of claim 13, wherein the inside surface of the (a) portion is temporarily joined to the surface of the (b) portion facing the inside surface of the (a) portion.

15. A fastening system for sanitary absorptive articles such as disposable diapers or napkins using the Z-shape pressure-sensitive adhesive tape of claims 1 or 2.

16. A sanitary absorptive article such as a disposable diaper or napkin having formed thereon the Z-shape pressure-sensitive adhesive tape of claims 1 or 2 through the pressure-sensitive adhesive layer of the (c) portion.

* * * * *